US009782124B2

(12) United States Patent
Nordstrom

(10) Patent No.: US 9,782,124 B2
(45) Date of Patent: *Oct. 10, 2017

(54) APPAREL FOR PHYSIOLOGICAL TELEMETRY DURING ATHLETICS

(71) Applicant: NIKE, Inc., Beaverton, OR (US)

(72) Inventor: Matthew D. Nordstrom, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/535,958

(22) Filed: Nov. 7, 2014

(65) Prior Publication Data
US 2015/0065843 A1 Mar. 5, 2015

Related U.S. Application Data

(63) Continuation of application No. 13/051,770, filed on Mar. 18, 2011, now Pat. No. 8,909,318.

(51) Int. Cl.
*A61B 5/00* (2006.01)
*A61B 5/024* (2006.01)
*A61B 5/0245* (2006.01)

(52) U.S. Cl.
CPC .......... *A61B 5/6804* (2013.01); *A61B 5/0002* (2013.01); *A61B 5/0006* (2013.01); *A61B 5/0245* (2013.01); *A61B 5/02438* (2013.01); *A61B 5/02444* (2013.01); *A61B 5/486* (2013.01); *A61B 5/6805* (2013.01); *A61B 2562/0209* (2013.01)

(58) Field of Classification Search
CPC ... A61B 5/6804; A61B 5/6802; A61B 5/6805; A61B 5/6823; A61B 5/6835
USPC ................................................. 600/388, 587
See application file for complete search history.

(56) References Cited

U.S. PATENT DOCUMENTS

| | | | |
|---|---|---|---|
| 5,100,713 A | 3/1992 | Homma et al. | |
| 5,610,877 A | 3/1997 | Adams et al. | |
| 6,001,749 A | 12/1999 | Child et al. | |
| 6,205,346 B1 | 3/2001 | Akiva | |
| 6,668,380 B2 | 12/2003 | Marmaropoulos et al. | |
| 6,895,261 B1 | 5/2005 | Palamides | |
| 7,070,571 B2 | 7/2006 | Kramer et al. | |
| 7,124,447 B2 | 10/2006 | Arganese | |
| 7,306,403 B1 | 12/2007 | Sanders | |
| 7,320,947 B2 | 1/2008 | Child et al. | |

(Continued)

OTHER PUBLICATIONS

Rakesh B. Katragadda and Yong Xu; A Novel Intelligent Textile Technology Based on Silicon Flexible Skins; Electrical and Computer Engineering, Wayne State University, Detroit, Michigan, MEMS 2007, Kobe, Japan, Jan. 2007, 4 pages.

(Continued)

*Primary Examiner* — Adam J Eiseman
(74) *Attorney, Agent, or Firm* — Shook, Hardy & Bacon L.L.P.

(57) ABSTRACT

A user interface component and system for physiological parameters telemetry is provided. A user interface component may be reversibly or irreversibly attached to a garment that allows connection to a user's skin, such as via one or more holes in the garment. Signals transmitted through a conductive transfer layer in the user interface component are provided to a signal receiving unit which can collect and transmit physiological data.

18 Claims, 8 Drawing Sheets

(56) References Cited

U.S. PATENT DOCUMENTS

| | | |
|---|---|---|
| 7,324,841 B2 | 1/2008 | Reho et al. |
| 7,635,439 B2 | 12/2009 | Child et al. |
| 7,684,755 B2 | 3/2010 | Pierce et al. |
| 7,783,334 B2 * | 8/2010 | Nam et al. .................... 600/388 |
| 7,793,361 B2 | 9/2010 | Ishihara et al. |
| 8,386,009 B2 * | 2/2013 | Lindberg et al. ............. 600/386 |
| 8,668,653 B2 | 3/2014 | Nagata et al. |
| 2003/0208830 A1 | 11/2003 | Marmaropoulos et al. |
| 2004/0051082 A1 | 3/2004 | Child |
| 2004/0053552 A1 | 3/2004 | Child et al. |
| 2004/0087228 A1 | 5/2004 | Van Heerden |
| 2005/0081913 A1 | 4/2005 | Ebbesen et al. |
| 2005/0095406 A1 | 5/2005 | Gunzel et al. |
| 2005/0096513 A1 | 5/2005 | Ozguz et al. |
| 2005/0217005 A1 | 10/2005 | DeSantis |
| 2006/0094948 A1 | 5/2006 | Gough et al. |
| 2006/0142654 A1 | 6/2006 | Rytky |
| 2006/0192184 A1 | 8/2006 | Child et al. |
| 2006/0196093 A1 | 9/2006 | Krauss |
| 2007/0038057 A1 | 2/2007 | Nam et al. |
| 2007/0073131 A1 | 3/2007 | Ryu et al. |
| 2007/0130676 A1 | 6/2007 | Von Blucher |
| 2007/0250981 A1 | 11/2007 | Seibert |
| 2007/0285868 A1 | 12/2007 | Lindberg et al. |
| 2007/0299325 A1 | 12/2007 | Farrell et al. |
| 2008/0091097 A1 | 4/2008 | Linti et al. |
| 2008/0096726 A1 | 4/2008 | Riley et al. |
| 2008/0125288 A1 | 5/2008 | Case |
| 2008/0256691 A1 | 10/2008 | White et al. |
| 2008/0287769 A1 | 11/2008 | Kurzweil et al. |
| 2009/0047481 A1 | 2/2009 | Welsch et al. |
| 2009/0049871 A1 | 2/2009 | Klett et al. |
| 2009/0088652 A1 | 4/2009 | Tremblay |
| 2009/0112078 A1 | 4/2009 | Tabe |
| 2009/0204013 A1 | 8/2009 | Mühlsteff et al. |
| 2009/0227857 A1 | 9/2009 | Rowe et al. |
| 2010/0010379 A1 | 1/2010 | De Rossi et al. |
| 2010/0077528 A1 | 4/2010 | Lind et al. |
| 2010/0130846 A1 | 5/2010 | Rytky |
| 2010/0185076 A1 | 7/2010 | Jeong et al. |
| 2010/0198043 A1 | 8/2010 | Holzer et al. |
| 2010/0234715 A1 | 9/2010 | Shin et al. |
| 2012/0165645 A1 * | 6/2012 | Russell et al. ................ 600/388 |

OTHER PUBLICATIONS

International Search Report and Written Opinion dated Jul. 11, 2012 in Application No. PCT/US12/29448, 11 pages.

Non-Final Office Action dated Sep. 11, 2013 in U.S. Appl. No. 13/051,770, 12 pages.

Final Office Action dated Dec. 17, 2013 in U.S. Appl. No. 13/051,770, 12 pages.

Notice of Allowance dated Aug. 5, 2014 in U.S. Appl. No. 13/051,770, 12 pages.

European Office Action date Jan. 5, 2016 in Application No. 12761274.5, 3 pages.

* cited by examiner

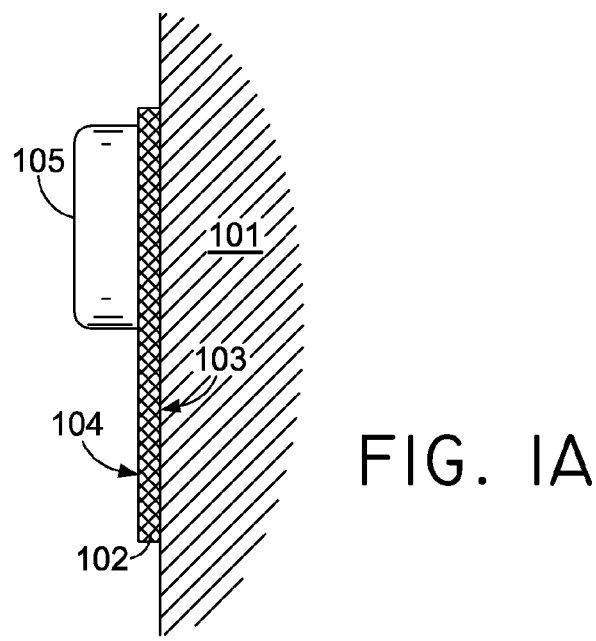
FIG. IA
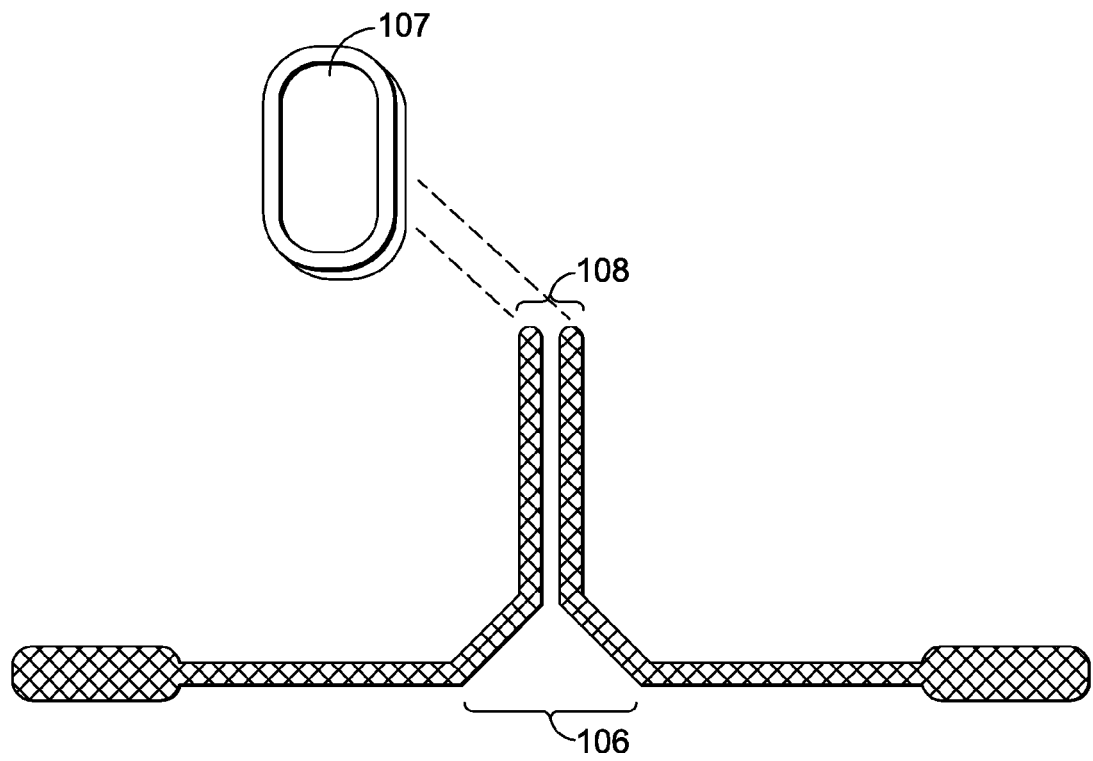
FIG. IB

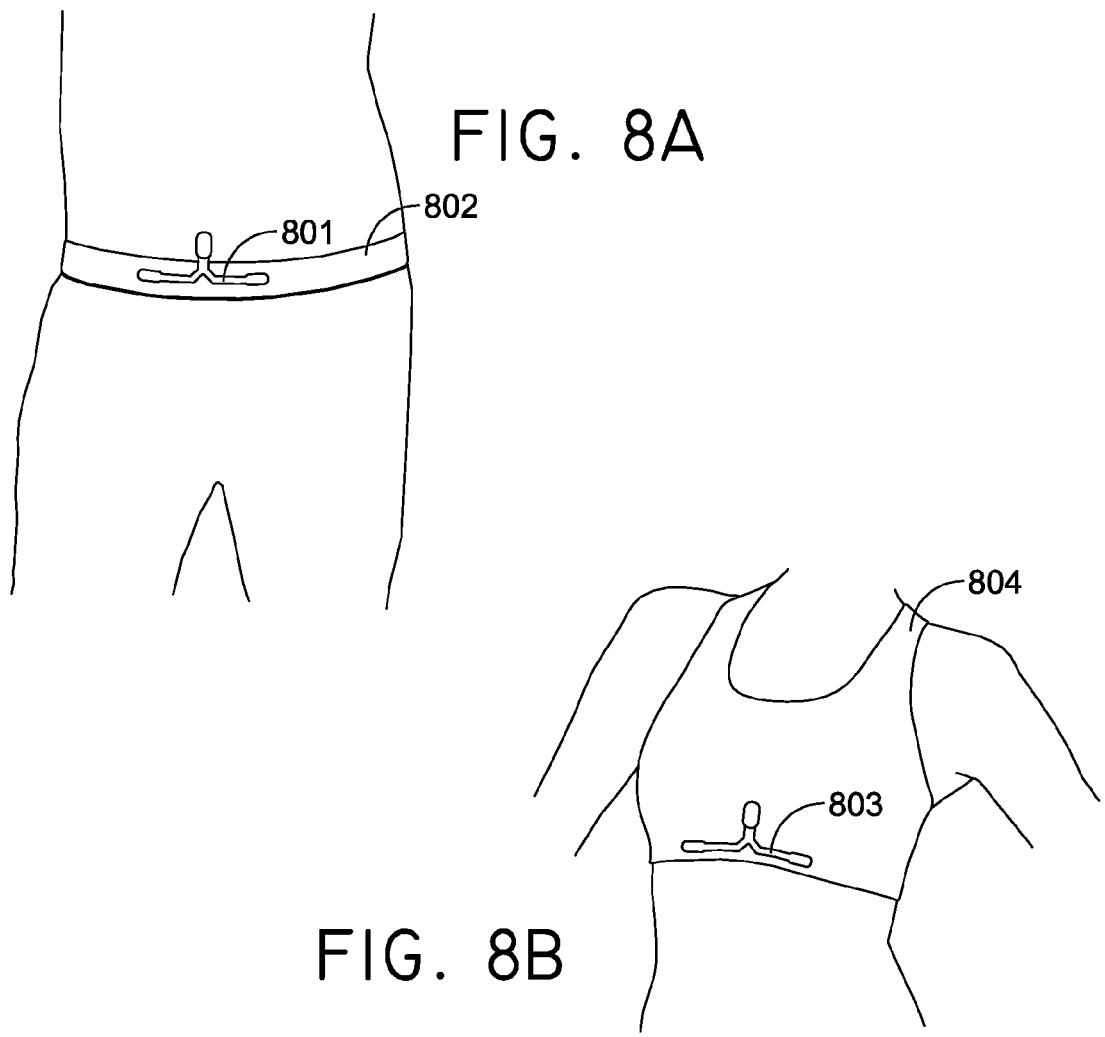
FIG. 8A
FIG. 8B
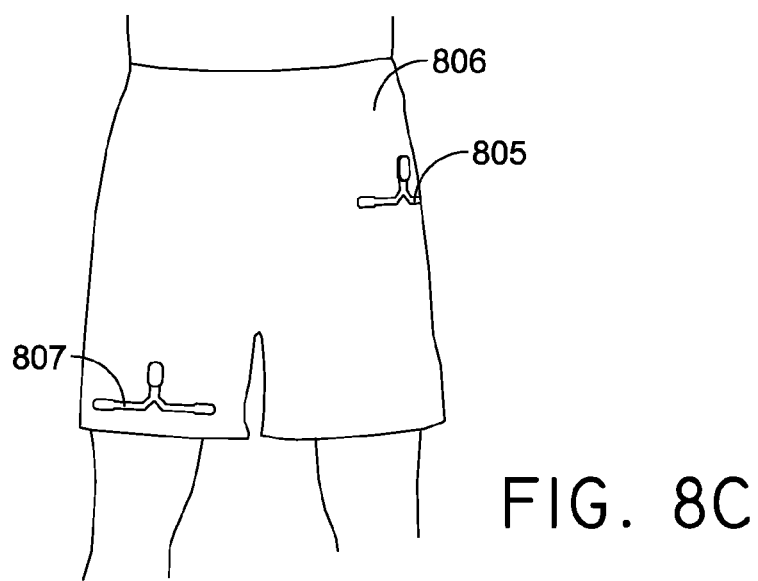
FIG. 8C

APPAREL FOR PHYSIOLOGICAL TELEMETRY DURING ATHLETICS

CROSS-REFERENCE TO RELATED APPLICATIONS

This application referenced by U.S. application No. 14/535,958 and entitled "Apparel for Physiological Telemetry During Athletics" is a Continuation application of co-pending U.S. application Ser. No. 13/051,770, filed Mar. 18, 2011 and entitled "Apparel for Physiological Telemetry During Athletics." The entirety of the aforementioned application is incorporated by reference herein.

FIELD

The present disclosure relates to telemetry of physiological data.

BACKGROUND

During exercise or activity, physiological parameters of an athlete or other individual may fluctuate. Tracking these physiological parameters can provide important data in the study of athletic performance. Monitoring physiological parameters during exertion can be a useful route to optimizing performance and safeguarding the health of an athlete.

SUMMARY

Accordingly, many approaches to monitoring physiological parameters of an athlete are obtrusive and cumbersome, which can discourage use by athletes and other users. For example, a conventional heart rate monitor may require a strap encircling the chest of the wearer that some athletes may find uncomfortable or restrictive during training or competition. Some types of conventional physiological data collection devices may not be practical to wear during athletic training or competition at all. Moreover the amount and types of parameters or data that may be monitored or collected with conventional data collection devices may be limited due to the added weight and dimension of additional conventional monitoring devices. However, collecting physiological data during athletic training and/or competition can provide valuable insights to maximize the benefits of training while minimizing the risk of overtraining and injury. An apparel telemetry heat transfer device or component is presented herein that is easily integrated into apparel and provides less conspicuous athlete telemetry.

In one example, a system for physiological parameters telemetry is provided comprising at least one user interface component comprising at least one conductive transfer layer having a bottom side and a top side, such that at least a portion of the bottom side of the conductive transfer layer is adapted to contact a user's skin. The system also comprises at least one signal receiving unit connected to the top side of the at least one conductive transfer layer and a garment having a back side contacting the user's skin and a face side. The garment is adapted to receive the at least one signal receiving unit at the face side and is further adapted to receiving the at least one user interface component on at least one of the face side or the back side. In one example, the garment may comprise one or more holes exposing the user's skin such that the portion of the bottom side of the user interface component contacts the user's skin at the one or more holes. In another example, the top side of the user interface component is on the back side of the garment.

In additional examples, the at least one user interface component of the system may comprise a bottom insulating layer contacting the bottom side and isolating at least a portion of the bottom side of the at least one conductive transfer layer from the face side of the garment. The at least one user interface component may also comprise a top insulating layer contacting the top side of the at least one conductive transfer layer. The at least one user interface component may comprise an adhesive layer at least in part between the bottom insulating layer and the face side of the garment. In one example, the garment may be a shirt and the one or more holes may be located at the chest area of the shirt. The conductive transfer layer may be an electrically conductive heat transfer layer.

In another example, a user interface component for physiological parameters telemetry is provided, the component comprising at least one conductive transfer layer having a bottom side and a top side and at least a portion of the bottom side is adapted to contact a user's skin through one or more holes in a garment, the garment having a face side and a back side. The user interface component may also comprise a bottom insulating layer contacting the bottom side of the at least one conductive transfer layer and isolating at least a portion of the bottom side of the at least one conductive transfer layer from the face side of the garment. The user interface component may also comprise a top insulating layer contacting the top side of the at least one conductive transfer layer.

Additionally, the user interface component may comprise an adhesive layer at least in part between the bottom insulating layer and the face side of the garment. The user interface component may have the bottom insulating layer bonded to the face side of the garment. Furthermore, the at least one conductive transfer layer may be an electrically conductive heat transfer layer. The at least one conductive transfer layer may comprise a metal or the at least one conductive transfer layer may comprise a carbon material. The garment may be a shirt and the one or more holes, through which the portion of the bottom side of the conductive transfer layer contacts a user's skin, may be located at a chest area of the shirt.

In one example, a user interface component for physiological parameters telemetry is provided, the component comprising at least one conductive transfer layer having a bottom side and a top side and at least a portion of the bottom side is adapted to contact a user's skin when attached to a garment worn by the user, the garment having a face side and a back side. The user interface component may also comprise a bottom insulating layer contacting the bottom side of the at least one conductive transfer layer and isolating at least a portion of the bottom side of the at least one conductive transfer layer. The user interface component may also comprise a top insulating layer contacting the top side of the at least one conductive transfer layer.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 1A-B illustrate different views of one example of a user interface component.

Figure 2:
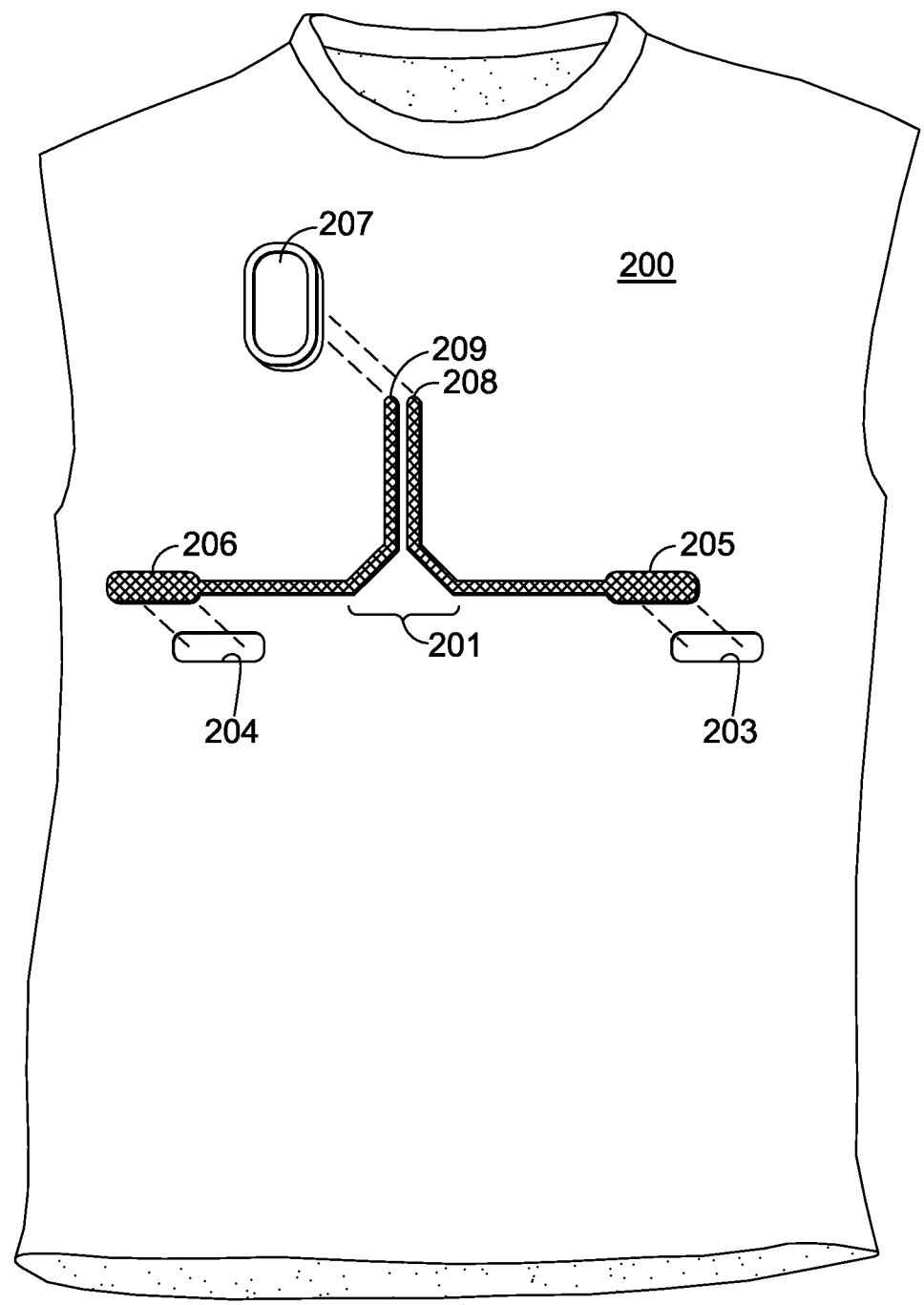
FIG. 2 illustrates one example of a system for physiological parameters telemetry.

FIGS. 8A-C illustrates additional garments incorporated into a physiological parameters telemetry system.

Corresponding reference numerals indicate corresponding parts throughout the several views of the drawings.

DETAILED DESCRIPTION

Referring to FIG. 1A, one example of a user interface component for physiological parameters telemetry is depicted. A user interface component may comprise at least one conductive transfer layer 102 and a signal receiving unit 105 connected to the at least one conductive transfer layer 102. The conductive transfer layer 102 may have a top side 104 and a bottom side 103. Generally, at least a portion of the bottom side 103 of the at least one conductive transfer layer 102 contacts a user's skin 101. Thermal and/or electrical signals may propagate through the at least one conductive transfer layer 102 and be received by the signal receiving unit 105. FIG. 1B illustrates one example of a user interface component 106. The "inverted-T" shape of the user interface component 106 is merely exemplary. Additional shapes of the user interface component and conductive transfer layers may be employed for various locations of a user's body or to accommodate measurement of varying physiological data. The signal receiving unit 105 transmits the collected physiological parameters data to one or more external recording or computing sources. The signal receiving unit 105 may transmit signals in any form using any useful data transfer formats or protocols. For example, signals may be relayed to external sources by radio transmissions and/or cellular telephone transmissions. Signals may utilize 802.11 protocols, Bluetooth, etc. In one example, the signal receiving unit 105 is connected to a portion of the user interface component. The signal receiving unit 105 may also store data for later downloading or transmission through either a wireless or wired connection. Furthermore, the signal receiving unit 105 may be removable so that the user interface component may be launderable without compromising electronics within the signal receiving unit 105.

One example of a conductive transfer layer may use a silver or silver impregnated substrate to provide conductivity of electric and/or thermal signals. In another example, carbon is used as the conductive material. Alternately or in conjunction, a conducting polymer or other organic material is employed as a conductive portion of the conductive transfer layer. For example, electrically conductive fabric or fibers may be incorporated into a conductive transfer layer. It may be advantageous to include a plurality of materials in order to transmit different physiological signals.

FIG. 2 illustrates one example of a user interface component incorporated into a system for physiological parameters telemetry. A system for physiological parameters telemetry may include a shirt 200 or other garment or accessory worn such that at least a portion touches the user's skin. A compressive shirt or other compressive garment may be incorporated into a system for physiological parameters telemetry to assure sufficient contact with the user's skin to make measurements. In another example, the system may be incorporated into a belt or sport bra. The example of the shirt 200 includes one or more holes 203, 204 through the fabric of the shirt to provide an area for the conductive transfer layer 205 to contact the user's skin. The holes 203, 204 illustrated in FIG. 2 are not necessarily to scale with the shirt 200. The holes may be of varying size and location to accommodate the user interface component. For example, one or more holes for contact may be in the chest area of a garment and/or the armpit areas of a garment and/or back areas. For some applications, a micro-scale user interface component may be employed, and the contact area to the user's skin provided by the holes may be scaled accordingly. In another example, the garment itself may use conductive portions to bridge between the user's skin and the user interface component so that direct contact of the user's skin with the user interface component is minimized.

Returning to FIG. 2, a portion of the conductive transfer layer contacts the user's skin through holes 203, 204 in the garment 200. Another portion of the conductive transfer layer 208, 209 contacts the signal receiving unit 207. The signal receiving unit 207 receives thermal and electrical signals collected from the user through the conductive transfer layer and relays them to various external data collection and analysis units. The user interface component may be removable from the garment 200 and may include a plurality of materials to provide one or more conductive transfer layers. The user interface component may be stitched, bonded, or adhered to the garment to provide stability while being worn by the user. The signal receiving unit 207 may also be separated from the system. The signal receiving unit may be held in place by any means, including stitching, bonding, apparel closures such as snaps or hook-and-eye closures, or using magnetic closures.

Examples of electronic modules that may be incorporated into the signal receiving unit or the sensor are illustrated in U.S. patent application Ser. No. 11/416,458, published as U.S. Patent Application Publication No. 2007/0260421, the entirety of which is incorporated by reference herein and made part of hereof. Aspects of the invention may relate to U.S. patent application Ser. No. 11/166,351, published as U.S. Patent Application 2007/0011919, and also U.S. patent application Ser. No. 11/848,988, patented as U.S. Pat. No. 7,771,320, both of which are incorporated by reference herein and made part of hereof.

Figure 3:
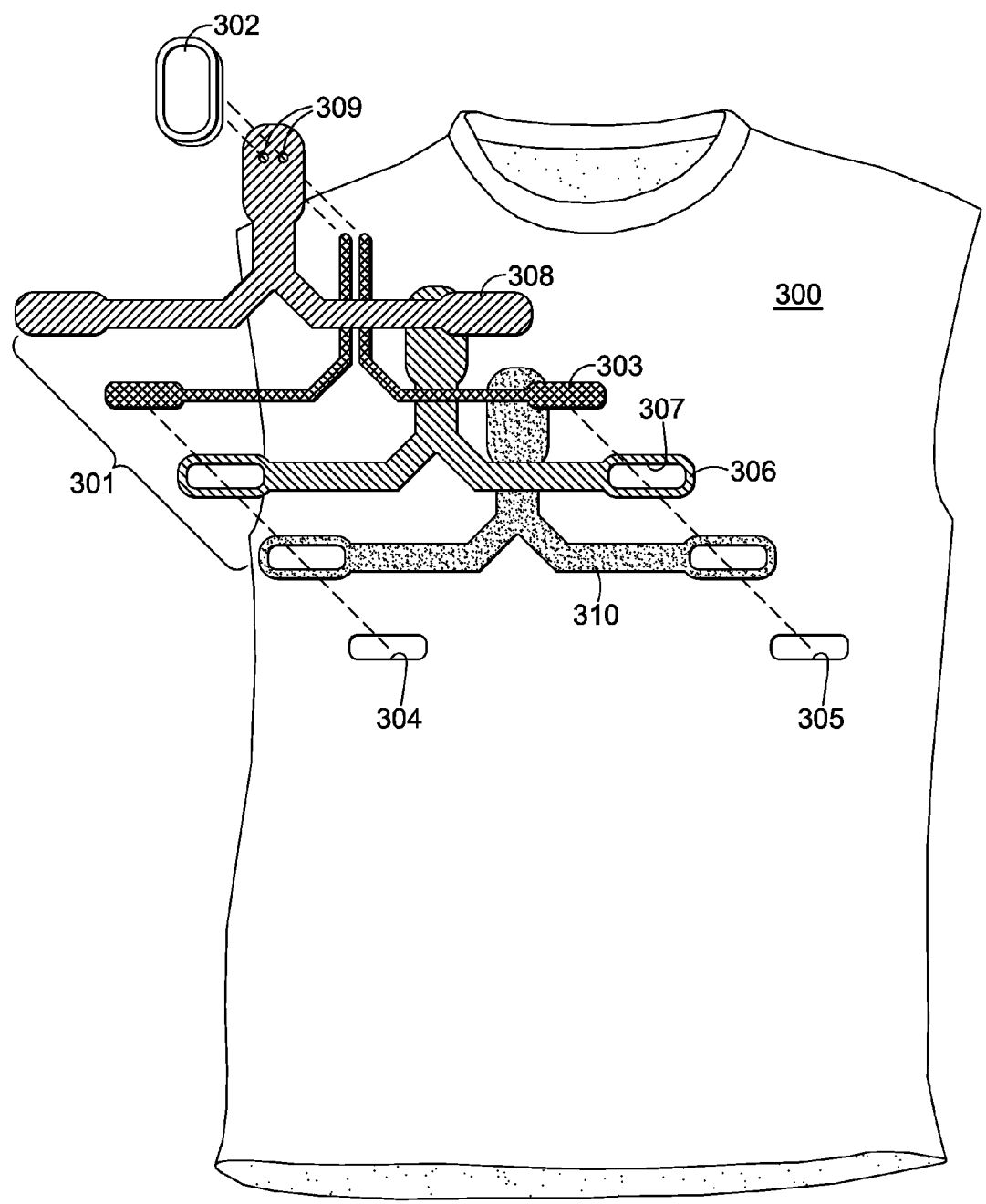
FIG. 3 illustrates another example of a system for physiological parameters telemetry.

FIG. 3 illustrates an additional example of user interface component and system for physiological parameters telemetry. The user interface component 301 may comprise a conductive transfer layer 303. The conductive transfer layer 303 may be an electrically conductive heat transfer layer. The conductive transfer layer 303 contacts a portion of the user's skin through one or more holes 304, 305 in a garment 300. The conductive transfer layer 303 also contacts at least one signal receiving units 302. Additionally, the user interface component 301 may include a bottom insulating layer 306 contacting the conductive transfer layer 303 on the bottom side and isolating or insulating a portion of the bottom side of the conductive transfer layer 303 from the garment 302. The bottom insulating layer 306 also provides an exposed region 307 for the conductive transfer layer to line up with the holes 304, 305 provided in the garment 300 for contacting the user's skin.

The user interface component 301 may also have a top insulating layer 308 contacting the top side of the conductive transfer layer 303. The top insulating layer 308 may protect the conductive transfer layer 303 from environmental contamination and/or damage. The top insulating layer 308 may also have a point of contact 309 to expose the conductive transfer layer 303 and allow the signal receiving unit 302 to connect with the conductive transfer layer 303. The top insulating layer 308 may possess decorative elements. While the top insulating layer 308, the conductive transfer layer 303, and the bottom insulating layer 306 are illustrated as three separate layers, a plurality of layers may be used for any individual layer. In addition, the top insulating layer 308 and the bottom insulating layer 306 may be formed of one material and encapsulate the conductive transfer layer 303.

There may also be provided an adhesive layer 310 on either the garment or on the garment facing side of the bottom insulating layer 306 or directly on the conductive transfer layer 303. The adhesive layer 310 and the bottom insulating layer 306 may be the same layer. The adhesive layer 310 may be provided to any portion of the user interface component 301. The adhesive layer 310 may have glue or other bonding medium to provide robust attachment of the user interface component 301 to the garment 300. The adhesive layer 310 may have a reversible or irreversible attachment mechanism. Alternately or in conjunction, conventional apparel fasteners, such as hook-and-eye closures, buttons, or snaps, may be employed to attach the user interface component 301 to the garment 300.

Figure 4:
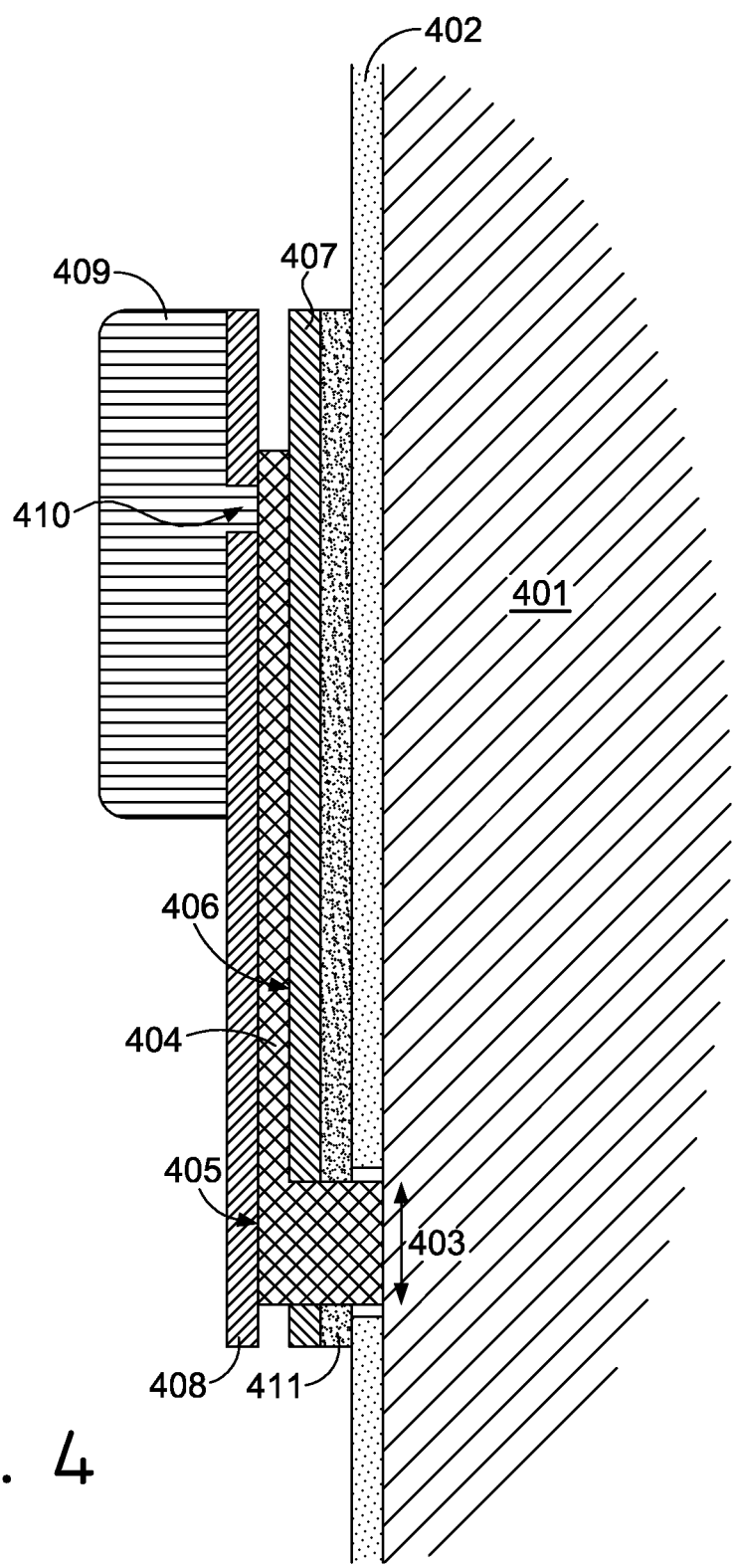
FIG. 4 illustrates an additional view of a system for physiological parameters telemetry.

FIG. 4 illustrates a side view of one example of a system for physiological parameters telemetry. Generally, the user interface component may comprise a conductive transfer layer 404 having a top side 405 and a bottom side 406. A portion of the bottom side 406 may contact the user's skin 401. In FIG. 4, a user's skin 401 is illustrated with a fabric or other garment layer 402. The fabric or other garment layer 402 may lie substantially between the user interface component and the user's skin 401. However, the garment or fabric 402 may include at least one hole so that a portion 403 of the conductive transfer layer 404 may contact the user's skin. While FIG. 4 shows direct contact between the conductive transfer layer 404 and the user's skin 401, there may be additional intervening conductive materials or layers. For example, a conductive adhesive or lubricant may be applied to the conductive transfer layer or the user's skin. In another example, the hole in the garment 402 may be supplemented with a conductive polymer impregnated into the fabric so that direct contact of the user's skin can be avoided. The garment itself may be wholly or partially constructed of a thermal and/or electrically conductive material, in which case, the user interface component may be connected with the user skin via the bridge provided by the conductive garment. The system in FIG. 4 may further comprise a signal receiving unit 409 that contacts 410 the conductive transfer layer 404.

The garment 402 may have a back side against the user's skin and a face side away from the user's skin. The garment 402 worn by the user with at least one hole 403 provided such that the conductive transfer layer 404 contacts a portion of the user's skin 401. In one example, the garment may be a compressive shirt and one or more holes may be in the chest area of the compressive shirt. The conductive transfer layer may have a bottom side 406 and a top side 405. The bottom side of the conductive transfer layer 406 may contact the user's skin. The bottom insulating layer 407 may contact at least a portion of the bottom side 406 of the conductive transfer layer 404. The bottom insulating layer 407 may protect the bottom side 406 of the conductive transfer layer 404 from the user's body and environment. The adhesive layer 411 may allow robust attachment of the bottom insulating layer 407 to the face side of the garment 402. The adhesive layer 411 may cover all or a portion of the bottom insulating layer 407. The adhesive layer 411 may also be applied to the conductive transfer layer 404 while leaving a portion 403 of the conductive transfer layer 404 exposed to allow contact with the user's skin 401. At least a portion of the conductive transfer layer 404 may be exposed by the bottom insulating layer to allow contact with the user's skin 401.

The top insulating layer 408 contacts a portion of the top side 405 of conductive transfer layer 404 and may provide protection for the conductive transfer layer 404 from the user's environment. The top insulating layer 408 may include a region where the top side 405 of the conductive transfer layer 404 is partially exposed to provide at least one contact point 410 for at least one signal receiving unit 409. While it is illustrated that each layer is in direct contact, the layers may include intervening sublayers and/or other components to bridge the connections or provide other functionality.

Figure 5:
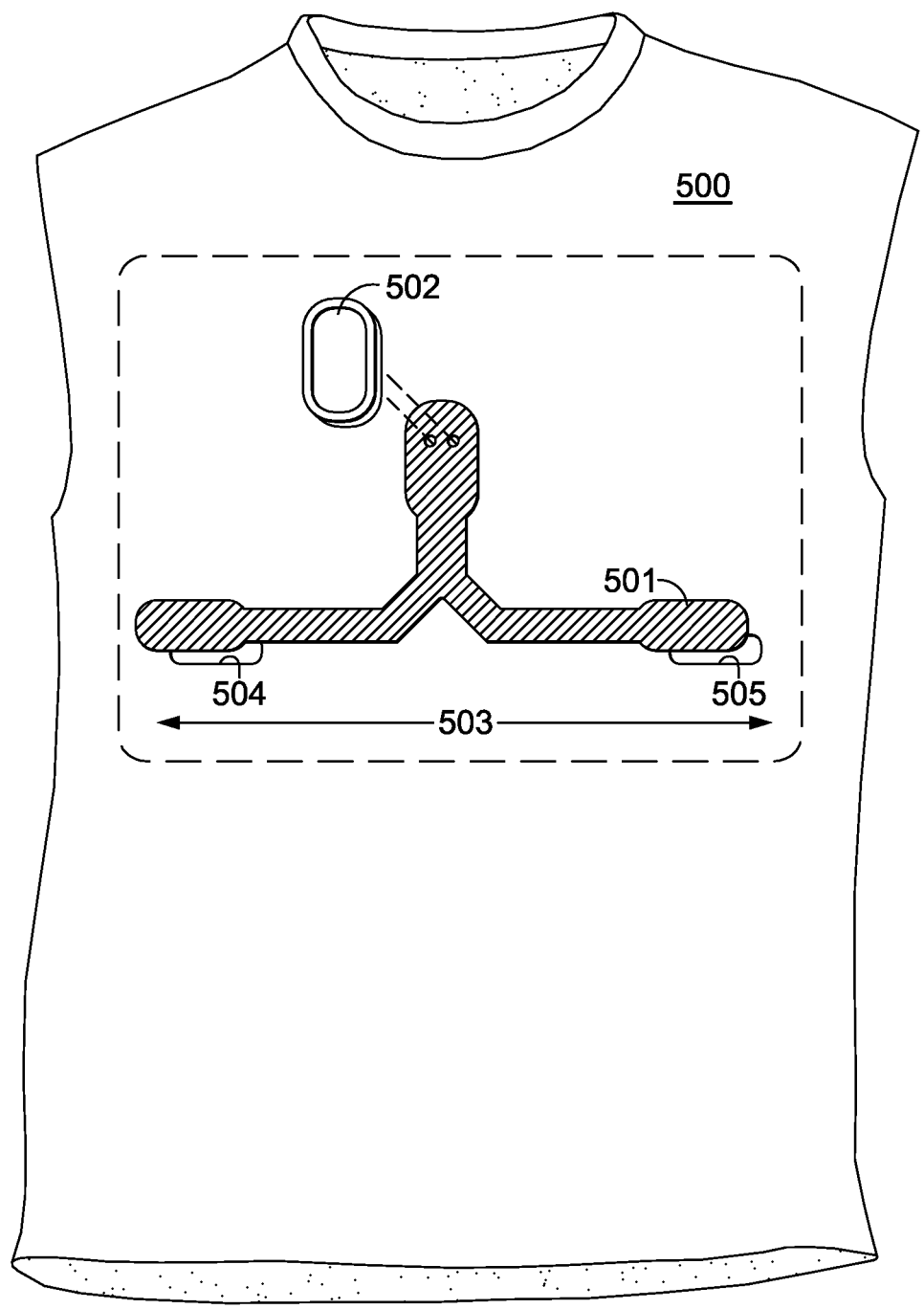
FIG. 5 illustrates a side view example of a physiological parameters telemetry system.

FIG. 5 illustrates one example of a system for physiological parameters telemetry. The garment 500 may be a shirt as illustrated but may be any garment or accessory worn in close fit with the user's skin. One or more user interface components 501 may be appliquéd to the surface of the garment 500. As illustrated, the user interface component 501 is not to scale with the garment. The user interface component 501 may have any size ratio in comparison with the garment, which is particularly advantageous as the dimensions of the user interface component 501 may be determined by the physiological parameters to be collected. In FIG. 5, the user interface component 501 is located in a chest area 503 of the garment 500 and the holes 504, 505 in the garment provided for the conductive transfer layer to contact the user's skin are located in the chest area 503. While it is illustrated that a user interface component is located in a chest area, the user interface component may be located anywhere on the garment. For example, it may be useful to include user interface component(s) at the armpit and/or back regions. While it is illustrated that there is one user interface component to one signal receiving unit, any ratio of user interface components to signal receiving units may be utilized in a system for physiological parameters telemetry. For example, it may be useful to have multiple user interface components connected to a single signal receiving unit. Alternately or in conjunction, a single user interface component may transmit a plurality of signals to a plurality of signal receiving units.

Figure 6:
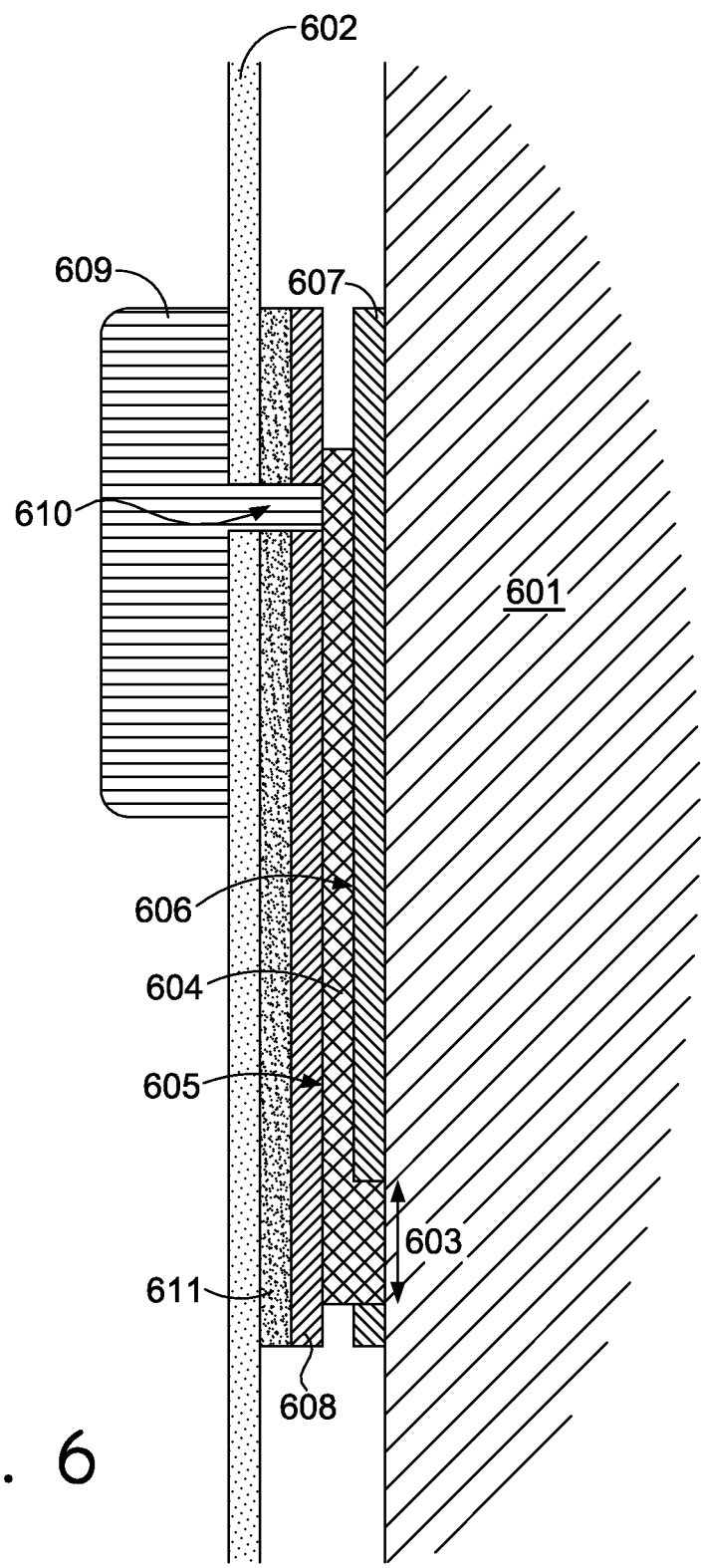
FIG. 6 illustrates a side view example of a physiological parameters telemetry system.

FIG. 6 illustrates an additional example of a system for physiological parameters telemetry in which the user interface component lies next to the user's skin such as on the inside of a garment, such as a compressive shirt or other form-fitting apparel. The user interface component may be bonded, stitched, or appliquéd to the back side of a garment. Another example might include a system in which the user interface component is embedded within the shirt. Generally, the user interface component may comprise a conductive transfer layer 604 having a top side 605 and a bottom side 606. A portion of the bottom side 606 may contact the user's skin 601. In FIG. 6, a fabric or other garment layer 602 illustrated with a user interface component that lies substantially between the fabric or other garment layer 602 and the user's skin 601. While FIG. 6 shows direct contact between the conductive transfer layer 604 and the user's skin 601, there may be additional intervening conductive materials or layers. For example, a conductive adhesive or lubricant may be applied to the conductive transfer layer or the user's skin. The system in FIG. 6 may further comprise a signal receiving unit 609 that contacts 610 the conductive transfer layer 604.

The garment 602 may have a back side against the user's skin and a face side away from the user's skin. The user interface component may be applied against the user's skin and attached to the back side of the garment 602. In one example, the garment may be a compressive shirt and one or more holes may be in the chest area of the compressive shirt. The conductive transfer layer may have a bottom side 606 and a top side 605. The bottom side of the conductive transfer layer 606 may contact the user's skin. The bottom insulating layer 607 may contact at least a portion of the bottom side 606 of the conductive transfer layer 604. The bottom insulating layer 607 may protect the bottom side 606 of the conductive transfer layer 604 from the user's body The top insulating layer 608 contacts a portion of the top side 605 of conductive transfer layer 604 and may lie substantially between the conductive transfer layer 604 and garment 602 or the back side of the garment. The top insulating layer 608 may include a region where the top side 605 of the conductive transfer layer 604 is partially exposed to provide at least one contact point 610 for at least one signal receiving unit 609. Contact through the face side and the back side of the garment to the user interface component may be provided by small holes or other conductive bridging materials. While it is illustrated that each layer is in direct contact, the layers may include intervening sublayers and/or other components to bridge the connections or provide other functionality The adhesive layer 611 may allow robust attachment of the top insulating layer 608 to the back side of the garment 402. The adhesive layer 611 may cover all or a portion of the top insulating layer 608. The adhesive layer 611 may also be applied to the conductive transfer layer 604 to adhere the conductive transfer layer to the back side of the garment. At least a portion 603 of the conductive transfer layer 604 may be exposed by the top insulating layer 608 to allow contact with the signal receiving unit.

Figure 7:
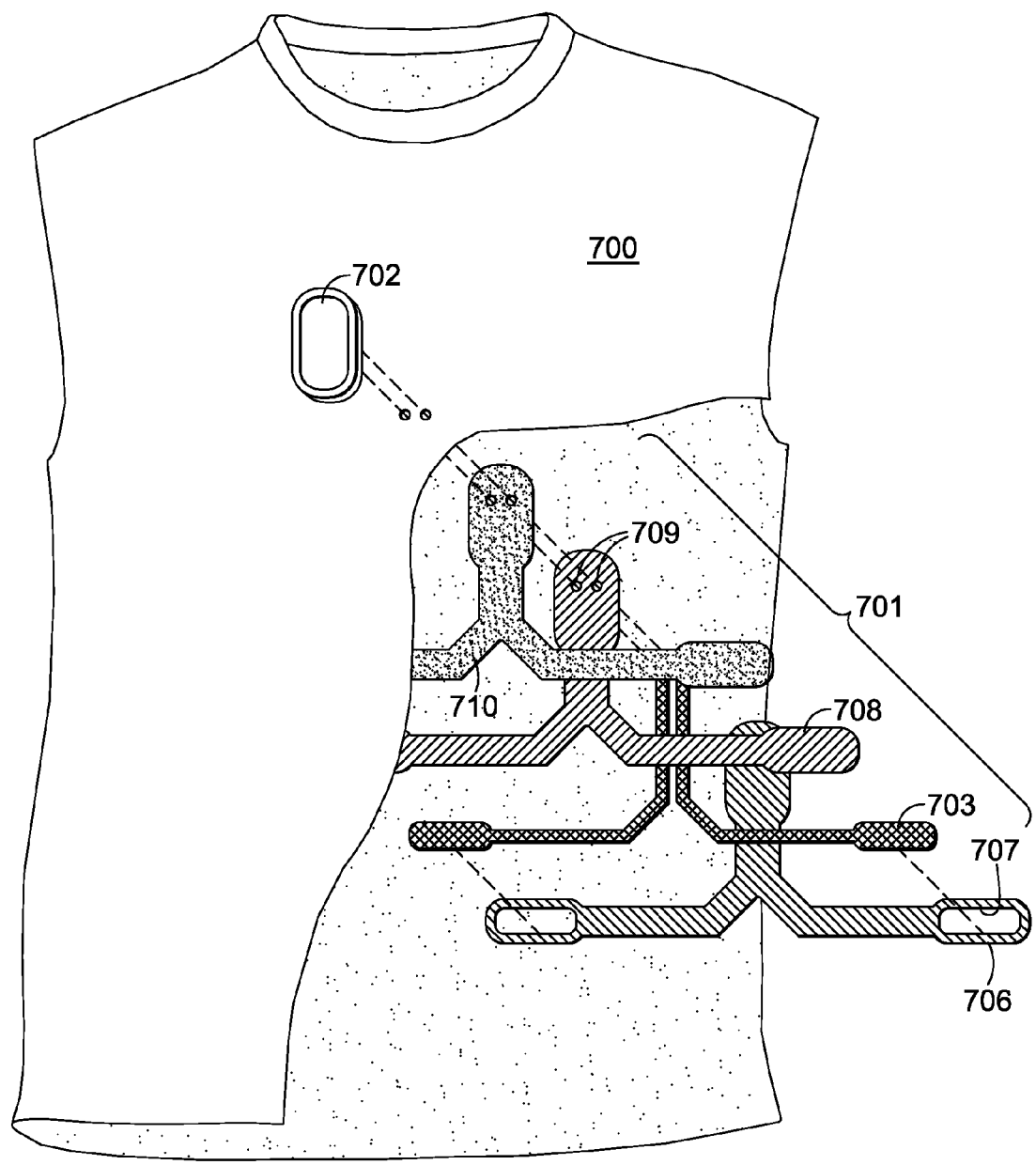
FIG. 7 illustrates an additional example of a physiological parameters telemetry system.

FIG. 7 illustrates an additional example of user interface component and system for physiological parameters telemetry. The user interface component 701 may comprise a conductive transfer layer 703. The conductive transfer layer 703 may be an electrically conductive heat transfer layer. The conductive transfer layer 703 contacts a portion of the user's skin and lies substantially between the garment and the user's skin. The conductive transfer layer 703 also contacts at least one signal receiving units 702. Additionally, the user interface component 701 may include a bottom insulating layer 706 contacting the conductive transfer layer 703 on the bottom side and isolating or insulating a portion of the bottom side of the conductive transfer layer 703 from the user's skin. The bottom insulating layer 706 also provides an exposed region 707 for contacting the user's skin.

The user interface component 701 may also have a top insulating layer 708 contacting the top side of the conductive transfer layer 703. The top insulating layer 701 may lie substantially between the garment or fabric and the conductive transfer layer 703. The top insulating layer 708 may also have a point of contact 709 to expose the conductive transfer layer 703 and allow the signal receiving unit 702 to connect with the conductive transfer layer 703. While the top insulating layer 708, the conductive transfer layer 703, and the bottom insulating layer 706 are illustrated as three separate layers, a plurality of layers may be used for any individual layer. In addition, the top insulating layer 708 and the bottom insulating layer 706 may be formed of one material and encapsulate the conductive transfer layer 703.

There may also be provided an adhesive layer 710 on either the garment or on the garment facing side of the top insulating layer 708 or directly on the top side of the conductive transfer layer 703. The adhesive layer 710 and the top insulating layer 708 may be the same layer. The adhesive layer 710 may be provided to any portion of the user interface component 701. The adhesive layer 710 may have glue or other bonding medium to provide robust attachment of the user interface component 701 to the garment 700. The adhesive layer 710 may have a reversible or irreversible attachment mechanism. Alternately or in conjunction, conventional apparel fasteners, such as hook-and-eye closures, buttons, or snaps, may be employed to attach the user interface component 701 to the garment 700.

FIGS. 8A-C illustrates additional examples of garments that are incorporated with a system for physiological parameters telemetry. FIG. 8A illustrates a user interface component 801 and signal receiving unit may be attached to a belt 802. FIG. 8B illustrates a user interface component and signal receiving unit 803 may be attached to a sport bra. FIG. 8C illustrates user interface components 805, 807 attached to a pair of shorts 803, particularly close-fitting bottoms such as undergarments or compressive shorts. The general locations illustrated in FIG. 8A-C are merely exemplary and further are not to scale. Locations for user interface components may vary according to the user and the physiological parameters to be monitors. A plurality of user interface components may be applied to areas of several garments to achieve comprehensive physiological telemetry.

A variety of physiological data may be obtained and transmitted by the described systems. Non-limiting examples of physiological parameters that may be monitored include: skin temperature, perspiration rate and for content, heart rate, blood pressure, heat flux, muscle contraction, etc. For example, skin temperature and/or core body temperature of an athlete at various levels of exertion and in different environments may be monitored. An athlete's pulse rate and/or blood pressure may be tracked as well. Respiratory rate statistics may be collected. Electrolyte loss via sweat may be monitored. Measurement and collection of different physiological data may include locating one or more user interface components at different areas of an athlete's body. For example, pulse rate may be measured near the carotid artery, the wrist, behind the knee or on the chest. In addition, the material and construction of the user interface component may be adjusted for the type of data to be collected. In an additional example, the user interface component may provide a conductive connection between the signal receiving unit and an additional unit connected with the user's skin. For additional sensing applications, it may be useful to provide a small current from the signal receiving unit having a power source to the user interface component.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and may be used in a selected embodiment, even if not specifically shown or described.

What is claimed is:

1. A system for physiological parameters telemetry, the system comprising:
   a garment having a skin-facing side and an outward-facing side, the garment configured to be worn by a user; and
   at least one user interface component located on the outward-facing side of the garment, the at least one user interface comprising at least:
      a conductive transfer layer having a first surface and a second surface, and a first terminal end and a second terminal end;
      a first insulating layer contacting the first surface of the conductive transfer layer, the first insulating layer having at least one aperture to allow at least a portion of the first surface of the conductive transfer layer to contact the user's skin;
      a second insulating layer having a first terminal end and a second terminal end, the second insulating layer contacting the second surface of the conductive transfer layer along the entire surface of the second surface of the conductive transfer layer except for at the first terminal end of the conductive transfer layer, wherein the first terminal end of the conductive transfer layer is oriented toward a head region of the user when the garment is being worn by the user, and wherein the first terminal end of the second insulating layer is generally aligned with the first terminal end of the conductive transfer layer; and
      a signal receiving unit adapted for connection to the conductive transfer layer second surface at the first terminal end of the conductive transfer layer.

2. The system of claim 1, wherein the garment is a shirt.

3. The system of claim 1, wherein the conductive transfer layer is an electrically conductive transfer layer.

4. The system of claim 1, wherein the first insulating layer is bonded to the outward-facing side of the garment.

5. The system of claim 1, wherein the first surface of the conductive transfer layer is adapted to contact the user's skin through an aperture in the garment when the garment is worn by the user.

6. The system of claim 5, wherein the at least one aperture of the first insulating layer is aligned with the aperture in the garment.

7. A physiological parameters telemetry system worn on a garment, the system comprising:
   a garment configured to be worn by a user;
   at least one user interface component comprising:
      a conductive transfer layer having a first surface and a second surface, and a first terminal end and a second terminal end, at least a first portion of the first surface adapted to contact the user's skin when the garment is worn by the user, wherein the first terminal end of the conductive transfer layer is oriented toward a head region of the user when the garment is worn by the user, and wherein the second terminal end of the conductive transfer layer is oriented toward a foot region of the user when the garment is worn by the user;
      a first insulating layer contacting at least a portion of the first surface of the conductive transfer layer, the first insulating layer having one or more apertures;
      a second insulating layer having a first terminal end and a second terminal end, the second insulating layer contacting the second surface of the conductive transfer layer along the entire surface of the second surface of the conductive transfer layer except for the first terminal end of the conductive transfer layer, wherein the first terminal end of the second insulating layer is generally aligned with the first terminal end of the conductive transfer layer; and
      a signal receiving unit adapted for connection to the conductive transfer layer second surface at the first terminal end of the conductive transfer layer.

8. The physiological parameters telemetry system of claim 7, wherein the first portion of the first surface of the conductive transfer layer is adapted to contact the user's skin via the one or more apertures of the first insulating layer.

9. The physiological parameters telemetry system of claim 7, wherein the first insulating layer is bonded to the garment.

10. The physiological parameters telemetry system of claim 9, wherein the first insulating layer is bonded to an outward-facing side of the garment.

11. The physiological parameters telemetry system of claim 7, wherein the conductive transfer layer is an electrically conductive heat transfer layer.

12. The physiological parameters telemetry system of claim 7, wherein the signal receiving unit is adapted to store physiological data.

13. A system for physiological parameters telemetry, the system comprising:
   a garment configured to be worn by a user, the garment having a skin-facing side and an outward-facing side, the garment having at least a first aperture;
   a user interface component located on the outward-facing side of the garment, the user interface component comprising:
      a conductive transfer layer having a first surface and a second surface, and a first terminal end and a second terminal end, wherein the first terminal end of the conductive transfer layer is oriented toward a head region of the user when the garment is worn by the user, and wherein the second terminal end of the conductive transfer layer is oriented toward a foot region of the user when the garment is worn by the user;
      a first insulating layer contacting the first surface of the conductive transfer layer, the first insulating layer having at least a second aperture that is aligned with the at least the first aperture of the garment to allow at least a portion of the first surface of the conductive transfer layer to contact the user's skin;
      a second insulating layer having a first terminal end and a second terminal end, the second insulating layer contacting the second surface of the conductive transfer layer along the entire surface of the second surface of the conductive transfer layer except for the first terminal end of the conductive transfer layer, the first terminal end of the second insulating layer generally aligned with the first terminal end of the conductive transfer layer; and
      a signal receiving unit adapted for connection to the conductive transfer layer second surface at the first terminal end of the conductive transfer layer.

14. The system of claim 13, wherein the garment comprises at least one of a shirt, a belt, or a sport bra.

15. The system of claim 13, wherein at least the first insulating layer and the second insulating layer are one of stitched, bonded, or adhered to the garment.

16. The system of claim 13, wherein the first insulating layer isolates at least a portion of the conductive transfer layer from the garment.

17. The system of claim 13, wherein the user interface component comprises one or more additional layers.

18. The system of claim 17, wherein at least one of the one or more additional layers comprises an adhesive layer.

* * * * *